US012605240B2

(12) United States Patent
Lamraoui et al.

(10) Patent No.: US 12,605,240 B2
(45) Date of Patent: Apr. 21, 2026

(54) SYSTEM FOR PROTECTING A SENSOR FOR A FORCE MEASUREMENT AND IMPLANTABLE OCCLUSION DEVICE COMPRISING SUCH A SYSTEM FOR PROTECTING THE SENSOR

(71) Applicant: UROMEMS, Grenoble (FR)

(72) Inventors: Hamid Lamraoui, Vaulnaveys le Haut (FR); Riaz Mir, Fontaine (FR); Marc Marien, La Tronche (FR); Clémentine Le Loc'h, Meylan (FR)

(73) Assignee: UROMEMS, Grenoble (FR)

( * ) Notice: Subject to any disclaimer, the term of this patent is extended or adjusted under 35 U.S.C. 154(b) by 889 days.

(21) Appl. No.: 17/911,847

(22) PCT Filed: Apr. 1, 2021

(86) PCT No.: PCT/FR2021/050578
§ 371 (c)(1),
(2) Date: Sep. 15, 2022

(87) PCT Pub. No.: WO2021/198622
PCT Pub. Date: Oct. 7, 2021

(65) Prior Publication Data
US 2023/0129458 A1 Apr. 27, 2023

(30) Foreign Application Priority Data
Apr. 1, 2020 (FR) ...................................... 2003237

(51) Int. Cl.
*A61F 2/00* (2006.01)
*G01L 1/26* (2006.01)
(52) U.S. Cl.
CPC ................ *A61F 2/004* (2013.01); *G01L 1/26* (2013.01); *A61F 2250/0003* (2013.01)

(58) Field of Classification Search
CPC ........................................... A61F 2/0031–0054
See application file for complete search history.

(56) References Cited

U.S. PATENT DOCUMENTS

| | | | |
|---|---|---|---|
| 5,287,757 A | 2/1994 | Polaert | |
| 2006/0211913 A1* | 9/2006 | Dlugos | ................. A61F 5/0003 600/37 |
| 2019/0274802 A1 | 9/2019 | Lamraoui | |

FOREIGN PATENT DOCUMENTS

WO 2016083428 A1 6/2016

OTHER PUBLICATIONS

Preliminary search report issued for the French priority application n° 2003237, mailed Dec. 18, 2020.
(Continued)

*Primary Examiner* — Thaddeus B Cox
(74) *Attorney, Agent, or Firm* — Thomas | Horstemeyer, LLP

(57) ABSTRACT

The invention relates to a system for protecting a sensor for a force measurement comprising:
  a force measurement sensor (1), designed to measure at least one tractive force or one compressive force exerted along a longitudinal axis (X) of the sensor, said sensor being designed to be made integral with a moveable part of a fluid reservoir, and
  a pre-strained elastic element (2) arranged to bias the force sensor (1) in a direction opposite to said exerted force, said elastic element being deformable in the direction of the exerted force so as to protect the sensor from at least one compressive or tractive force greater than a threshold.

20 Claims, 3 Drawing Sheets

(56)             References Cited

OTHER PUBLICATIONS

International search report issued for the corresponding PCT application n° FR2021/050578, mailed Jul. 20, 2021.

\* cited by examiner

SYSTEM FOR PROTECTING A SENSOR FOR A FORCE MEASUREMENT AND IMPLANTABLE OCCLUSION DEVICE COMPRISING SUCH A SYSTEM FOR PROTECTING THE SENSOR

CROSS REFERENCE TO RELATED APPLICATIONS

This application is the 35 U.S.C. § 371 national stage application of PCT Application No. PCT/FR2021/050578, filed Apr. 1, 2021, which application claims the benefit of French Application No. FR 2003237 filed Apr. 1, 2020, both of which are hereby incorporated by reference herein in their entireties.

FIELD OF THE INVENTION

The invention relates to a system for protecting a sensor for a force measurement, as well as an implantable hydraulic device comprising such a system for protecting the sensor.

PRIOR ART

Hydraulic medical devices exist intended to be implanted in a human or animal body to combat against erectile dysfunction or procuring a selective occlusion of an anatomical conduit, such as a urethra, a vesical neck, a colon, a rectum or a stomach for example.

Occlusion devices generally comprise a cuff surrounding said anatomical conduit and designed to exert a compression on said conduit.

The compression exerted by the cuff is controlled by an electromechanical control unit.

To enable a regulation of the pressure exerted on the conduit to occlude, the inflatable cuff is in fluidic connection with a fluid reservoir coupled to an actuator configured to inject fluid from the reservoir to the cuff (in order to increase the pressure exerted on the anatomical conduit) or from the cuff to the reservoir (in order to reduce the pressure exerted on the anatomical conduit). The assembly of the inflatable cuff, the reservoir and the fluidic connection between them form a fluidic circuit.

In such an occlusion system, it may be necessary to measure the pressure in the inflatable cuff or at another point of the fluidic circuit, for example to check the pressure when the actuator is de-activated, or instead to control the pressure exerted by said actuator.

The document WO 2016/083428 describes an implantable occlusion device which comprises a fluidic circuit including an inflatable occlusion cuff, a variable volume fluid reservoir comprising a fixed part and a moveable part, in fluidic connection with the cuff, and an actuator mechanically coupled to the moveable part of the reservoir so as to linearly displace said moveable part with respect to the fixed part to adjust the volume of the reservoir and thus induce a transfer of fluid between the reservoir and the cuff.

The actuator and the variable volume reservoir are arranged in a sealed housing containing a gas.

A force sensor arranged in the housing is mechanically connected to the moveable part of the reservoir to measure a tractive and/or compressive force in the direction of displacement of the moveable part of the reservoir.

The force measured by this sensor makes it possible to calculate the pressure in the fluidic circuit.

However, excessive loads applied to the sensor, notably in the event of rise in pressure in the reservoir, could damage it.

DESCRIPTION OF THE INVENTION

One aim of the invention is thus to conceive a system for protecting a sensor for the measurement of force in an implantable occlusion device making it possible to protect the force sensor against excessive loads.

To this end, a first subject matter of the invention relates to a system for protecting a sensor for a force measurement comprising:

- a force measurement sensor, designed to measure at least one tractive force or one compressive force exerted along a longitudinal axis of the sensor, said sensor being designed to be made integral with a moveable part of a fluid reservoir, and
- a pre-strained elastic element arranged to bias the force sensor in a direction opposite to said exerted force, said elastic element being deformable in the direction of the exerted force so as to protect the sensor from at least one compressive or tractive force greater than a threshold.

In a particularly advantageous manner, the system further comprises a stop, the force measurement sensor being moveable along said axis up to said stop in the direction of the force exerted counter to the biasing of the elastic element.

Preferably, the elastic element is pre-strained to a determined force value, designated pre-strained force, said pre-strained force being less than a maximum force being able to be withstood by the force measurement sensor, such that the force measurement sensor is designed to only be displayed towards the stop beyond said pre-strained force.

In certain embodiments, the system further comprises a toothed wheel integral with the force measurement sensor.

The system may further comprise a ball bearing integral with the force measurement sensor.

To protect the sensor against an excessive compressive force, the stop is arranged on a side of the force measurement sensor opposite to the fluid reservoir. Furthermore, the elastic element is arranged on a side of the force measurement sensor opposite to the fluid reservoir.

Conversely, to protect the sensor against an excessive tractive force, the stop is arranged on the same side of the force sensor as the fluid reservoir. Furthermore, the elastic element is arranged on the same side of the force measurement sensor as the fluid reservoir.

In a particularly advantageous manner, the elastic element is integral with the force measurement sensor in such a way as to make it possible to measure a tractive and/or compressive force by the force measurement sensor.

In certain embodiments, the pre-strained elastic element is a spring washer.

In a preferred embodiment, said spring washer is an elastic wave washer.

In certain embodiments, the force measurement sensor comprises an annular portion having a reduction in thickness, said portion being capable of bending under the application of an axial compressive or tractive force.

Advantageously, the force measurement sensor is bearing on the pre-strained elastic element by a peripheral portion external to the portion having the reduction in thickness.

In certain embodiments, the sensor comprises a strain gauge bonded on said annular portion having the reduction in thickness.

Another subject matter relates to a medical device designed to be implanted in a human or animal body, comprising:

(a) a fluidic circuit comprising:

an inflatable occlusion cuff containing a variable volume of a fluid, designed to surround at least one part of a natural conduit to occlude, a variable volume reservoir filled with a fluid, said reservoir comprising a fixed part and a moveable part, a fluidic connection between the reservoir and the occlusion cuff, (b) an actuator mechanically coupled to the moveable part of the reservoir so as to linearly displace said moveable part with respect to the fixed part to adjust the volume of the reservoir, the actuator and the variable volume reservoir being arranged in a sealed housing, (c) a system for protecting a sensor for a force measurement such as described above, the force measurement sensor being integral with the moveable part of the variable volume reservoir.

In certain embodiments, the moveable part of the variable volume reservoir is a gusset.

In a particularly advantageous manner, said gusset comprises a wall integral with a drive screw, said drive screw being coupled by a helical connection to a toothed wheel capable of being rotationally driven by the actuator, the force measurement sensor being arranged around the toothed wheel through a ball bearing.

In certain embodiments, the toothed wheel and the sensor are arranged in a gear box, the sensor being maintained against the elastic element by a fastening ring.

Another subject matter relates to a method for protecting a force measurement sensor designed to measure at least one tractive force or one compressive force exerted along a longitudinal axis of the sensor and to be made integral with a moveable part of a fluid reservoir, said method comprising at least the steps consisting in:

providing a system for protecting said sensor such as described above, exerting a tractive or compressive force along the axis of the sensor such that (i) as long as said force is less than the pre-strained force of the elastic element, the sensor deforms to measure the exerted force and (ii) when said force becomes greater than said pre-strained force, the sensor is displaced up to a stop.

In a particularly advantageous manner, the sensor reaches the stop when the exerted force is less than a force of deterioration of the sensor.

Furthermore, the sensor is only displaced towards the stop beyond the pre-strained force.

BRIEF DESCRIPTION OF THE FIGURES

Other characteristics and advantages of the invention will become clear from the detailed description that follows, with reference to the appended drawings, among which.

For reasons of legibility of the figures, the drawings are not necessarily made to scale.

DETAILED DESCRIPTION OF EMBODIMENTS

The implantable occlusion device comprises an inflatable occlusion cuff containing a variable volume of a fluid, intended to surround at least one part of a natural conduit to occlude, and a variable volume reservoir filled with a fluid.

Said reservoir comprises a fixed part and a moveable part, the displacement of the moveable part making the volume of the reservoir vary.

To this end, the occlusion device comprises an actuator mechanically coupled to the moveable part of the reservoir so as to linearly displace said moveable part with respect to the fixed part to adjust the volume of the reservoir. The actuator may notably comprise an electromagnetic motor and a reduction gear. The actuator is controlled by a device for controlling the pressure of the cuff implementing a force sensor of which the layout will be described below.

For each volume value of the reservoir, the moveable part has a known effective pressure surface, which may be constant or variable depending on the embodiments.

The occlusion device further comprises a fluidic connection (typically a tubing) between the reservoir and the occlusion cuff.

Thus, a variation in volume of the reservoir leads to an addition or a removal of fluid in the cuff, thus increasing or decreasing the compression exerted on the conduit surrounded by the cuff.

The assembly formed of the variable volume reservoir, the occlusion cuff and the fluidic connection is called fluidic circuit in the remainder of the description.

The device further comprises an energy source, rechargeable or not, making it possible to supply the different components. In a particular configuration, the energy source is outside of the human body and transmits energy wirelessly to the implanted device, for example by inductive coupling.

The variable volume reservoir, the actuator and, if needs be, the energy source, are arranged in a housing intended to be implanted in the body of the patient. The housing contains a gas, for example air. Said housing must be leak tight to avoid any transfer of fluid or gas from or to the intracorporal medium. The housing is made of a biocompatible material and may for example be produced from implantable titanium and sealed by laser welding. A leak tightness control may notably be carried out with helium to ensure the total leak tightness of the housing during the period for which the device is implanted.

Figure 1:
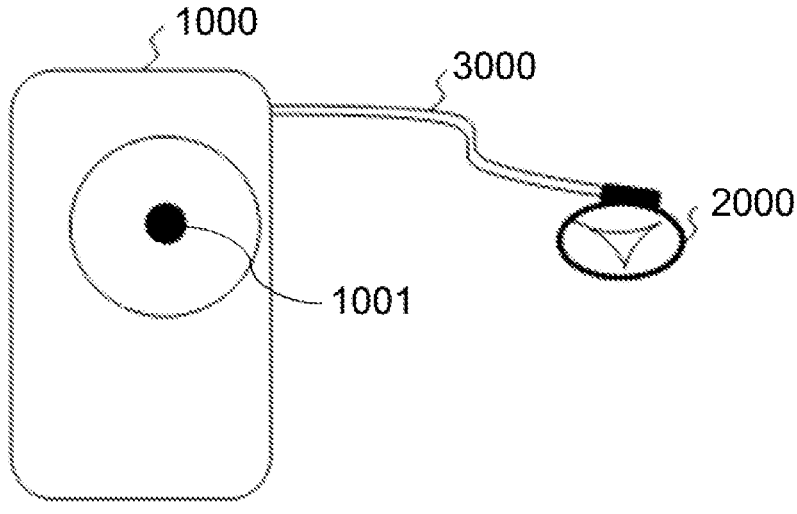
FIG. 1 is a schematic diagram of an implantable occlusion device.

FIG. 1 illustrates an implantable occlusion device comprising such a housing 1000, an occlusion cuff 2000 and a tubing 3000 connecting the variable volume reservoir situated inside the housing 1000 and the cuff 2000.

According to one embodiment, the housing may comprise a perforable puncture port 1001 arranged in a wall of the variable volume reservoir. A user can pierce said port by means of the needle of a syringe in order to add or, if necessary, remove fluid in the reservoir.

According to a preferred embodiment, the variable volume reservoir comprises a gusset assembled in the housing, the gusset and the housing being for example made of implantable titanium. The variable volume reservoir is then constituted of the gusset (serving as moveable part), a wall of the housing and a cover serving as, with said wall of the housing, fixed part. The reservoir further comprises an orifice making it possible to transfer fluid from and to the exterior of the reservoir.

The gusset has the advantage of ensuring total leak tightness of the implant while allowing the movement of the moveable wall. However, the present invention is not limited to the use of a gusset to form the variable volume reservoir. Thus, those skilled in the art will be able to implement a piston or a rolling or deformable membrane to produce the variable volume reservoir.

In the case of a gusset, the effective pressure surface is considered constant and is given by the manufacturer. For a rolling membrane, the effective pressure surface varies as a function of the position of the rolling membrane and is given by the manufacturer for different travel values. In the case of a piston sliding frictionlessly in a cylinder, the effective pressure surface is equal to the frontal surface of the piston.

The actuator may be chosen from among any electromechanical system making it possible to transform an electrical energy into a mechanical movement with the required power to enable the displacement at a force and at a required speed of the moveable part of the variable volume reservoir. Among actuators known to those skilled in the art may for example be cited piezoelectric actuators, electromagnetic motors with or without brushes (in the case of a brushless motor, said motor may be constituted of two poles or four poles) coupled or not to a reduction gear, electroactive polymers or instead shape memory alloys.

The housing also contains a sensor mechanically connected with the moveable wall of the variable volume reservoir so as to measure a compressive and/or tractive force in the direction of displacement of the moveable part of the reservoir. This sensor is hereafter called "force measurement sensor" or "force sensor". Unless stated otherwise, this sensor may be simply designated by the term "sensor" in the interest of brevity.

The force sensor is designed to deflect under the application of a compressive or tractive force. This deformation may be measured for example by means of a deformation gauge or strain gauge, and the force applied is determined from the deformation thus measured.

In a particularly advantageous manner, the sensor is mounted on an elastic element that biases it in a direction opposite to that of the compressive force. This elastic element procures two advantages. On the one hand, it makes it possible to protect mechanically the deflection of the force sensor in cases of application of an excessive compressive force, where the measurement of force is not necessarily desired. On the other hand, it makes it possible to optimise the sensitivity of the reading of the force measured by the sensor in the desired force range within the context of a normal usage of the device.

When it is wished to protect the sensor against an excessive tractive force, the elastic element is arranged to bias the sensor in a direction opposite to that of the tractive force.

If necessary, it is possible to protect the sensor against both excessive tractive and compressive forces by arranging two elastic elements on either side of the force sensor.

The elastic element is pre-strained to a determined force value, hereafter called "pre-strained force". This value is chosen to correspond to a force that is less than the maximum force that the sensor can withstand before being deteriorated, such that the sensor is only displaced beyond this pre-strained force to reach the stop and thus be protected against deterioration.

The position of the stop is determined as a function of the stiffness parameters of the elastic element, the desired pre-strained force, the maximum deformation of the sensor and so as to reach a force less than the maximum force necessary for the protection of the sensor in this position.

The fact of pre-straining the elastic element is particularly advantageous during the deformation of the sensor to avoid premature coming into contact with the stop while in a force measurement phase. Indeed, during the deformation of the sensor, the latter is placed very close to the stop with a possible contact, which could, in the absence of the elastic element, impact both the force measurement and/or adversely affect the displacement of the moveable part of the variable volume reservoir as explained hereafter.

Advantageously, such a system thus enables a reliable force measurement in a sufficient force range without deterioration of the sensor.

As long as the exerted force on the sensor is less than this value, only the sensor is deformed, which enables a direct measurement of the force.

If the force exerted on the sensor exceeds said value, the elastic element is compressed and the deformed sensor is displaced until reaching the stop. The measurement of force remains possible, but is less precise.

Once the stop reached, the sensor no longer deforms and the force measurement is thus no longer possible. However, in this position, the force sensor is protected since the stiffness constant of the spring, the pre-strained force of the spring, the deformation of the sensor and the distance travelled by the sensor beyond the determined force value are chosen and calculated so that the force undergone by the sensor is less than the maximum force that it can withstand before deteriorating.

In other words, it is possible to distinguish three operating phases of the sensor, in the sense of increasing compressive force.

In a first phase, the force exerted on the sensor (and measured by it) is comprised between zero and the pre-strained force, and the deflection of the sensor is comprised between zero and a first value noted X1. This first phase corresponds to a situation of normal usage of the device where it is wished to measure the force. The force measured by the sensor is thus low.

In a second phase, the force exerted on the sensor is comprised between the pre-strained force and a limit force, which is less than the maximum force that the sensor can undergo before deterioration, and the deflection of the sensor is comprised between X1 and a second value noted X2 (greater than X1). In this second phase, the force value measured by the sensor is less reliable than in the first phase. Due to this imprecision, it is not sought to measure the exerted force.

In a third phase, the force exerted on the sensor is greater than or equal to the limit force. The sensor having reached the stop, its deflection remains equal to X2.

In a particularly advantageous embodiment, the elastic element is in the form of a spring washer.

In certain embodiments, the spring washer is a wave washer. Such a washer is cut from a flat metal strip, for example steel or copper, then formed to have undulations. In the free state, non-strained, the washer has a height equal to the amplitude of the undulations. The wave washer is elastically deformable up to adopting a virtually flat shape.

The wave washer is preferred among the other types of spring washers for its compactness and its low stiffness.

In other embodiments, the spring washer is a Belleville type washer. Such a washer is cut out of a flat metal strip, for example steel or copper, then formed to have a truncated cone shape. In the free state, non-strained, the washer has a height equal to the distance between the base and the top of the truncated cone. The Belleville washer is elastically deformable up to adopting a virtually flat shape.

With respect to a helical spring or a combination of several helical springs, one advantage of the spring washer is that it has a reduced bulk while having a low stiffness meeting the desired force requirements for the measurement depending on the medical application. Furthermore, it exerts a uniform force on the sensor, which guarantees good precision of the force measurement while avoiding having parasitic loads in the measurement, which could for example be the case if a solution with several helical springs spread out at different emplacements of the circumference was implemented instead of the spring washer which covers all of the periphery.

Such a washer is thus particularly well suited to the miniaturisation constraints of an implantable device.

Figure 2A:
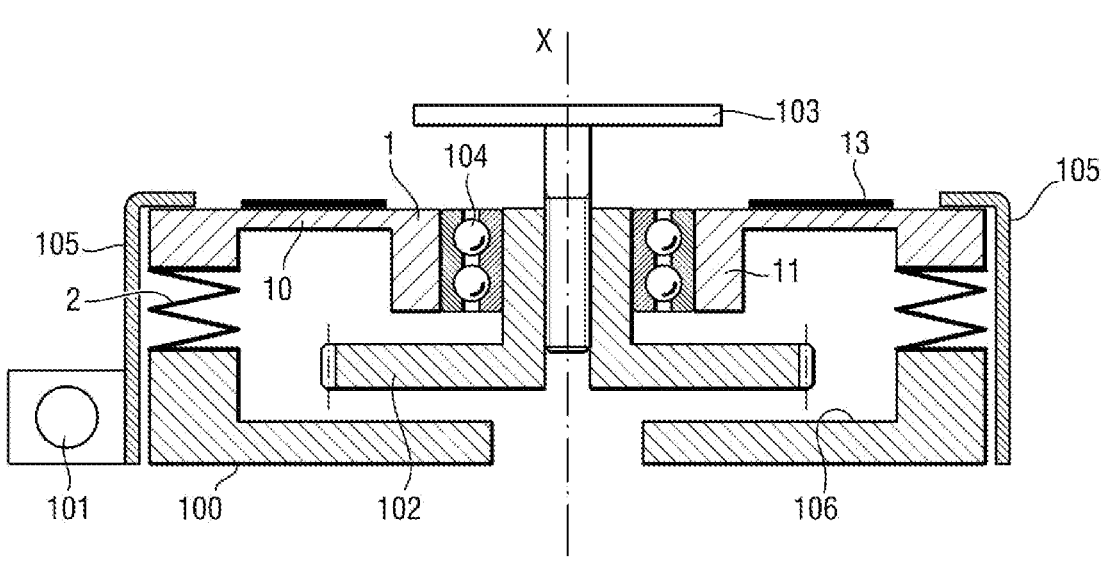
FIG. 2A is a schematic diagram of the security system of the force sensor in the free state.
Figure 2B:
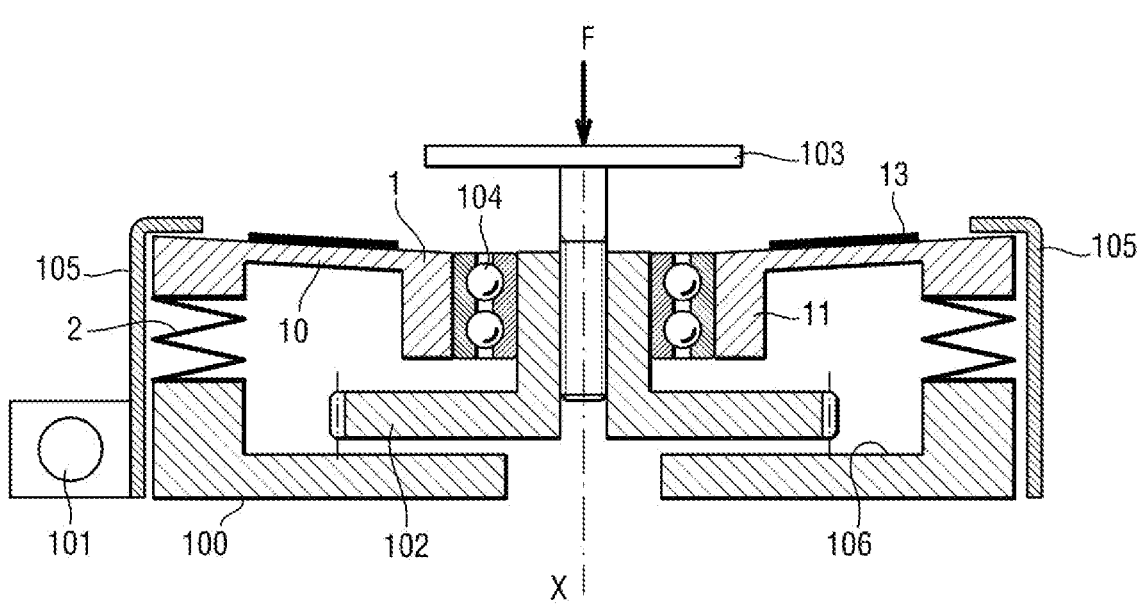
FIG. 2B is a schematic diagram of the security system of the force sensor of FIG. 2A subjected to a compressive force.

FIGS. 2A and 2B illustrate a schematic diagram of a part of the inside of the housing at the level of the actuator with the force sensor respectively in the free state, that is to say not subjected to a compressive force, and subjected to a compressive force.

The variable volume reservoir comprises a moveable part which, in this embodiment, is a gusset (not illustrated).

The gusset has a wall integral with a drive screw 103. For example, the end of the screw 103 comprises a flat flange which may be bonded on the wall of the gusset.

The housing further contains an actuator 101 comprising a motor coupled to a reduction gear.

The reduction gear is coupled to a toothed wheel 102 which is itself coupled to the drive screw 103 by a helical link. The rotation of the wheel 102 then translationally drives the drive screw along the axis X, which has the effect of displacing the wall of the gusset translationally along the axis X, the direction of displacement depending on the direction of rotation of the motor.

The force sensor 1 is arranged around the toothed wheel 102 through a ball bearing 104. The sensor is thus free vis-à-vis rotational movement.

The sensor has an annular shape, of which one portion 10 has a reduction in thickness which makes it capable of bending under the application of a force exerted along the axis X. The sensor comprises an annular strain gauge 13 in contact with the portion 10.

The sensor comprises a central shaft 11 having a through orifice for its assembly on the ball bearing 104.

The toothed wheel 102 and the force sensor 1 are housed in a gear box 100.

In this housing, the force sensor 1 is mounted between a spring washer 2 and a fastening ring 105. The fastening ring 105 closes the gear box 100 while enabling the passage of the drive screw 103 and maintains the force sensor in contact with the wave washer 2 while ensuring the desired pre-strain of the wave washer. In the embodiment illustrated, the spring washer is a wave washer but, in an alternative manner (not illustrated), the spring washer could be a Belleville washer.

The pre-strained wave washer 2 exerts on the force sensor a force along the axis X of direction opposite to that of a compressive force. This force may be expressed as the product of the stiffness of the washer multiplied by the difference in height resulting from a compression of the washer.

The connection between the force sensor 1 and the wave washer 2 is made at the level of a peripheral portion of the force sensor, external to the portion 10 which has the reduction in thickness. This peripheral portion is fixed as long as the force applied is less than the pre-strained force of the spring washer, whereas the central portion of the force sensor including a threading (not illustrated) is capable of being displaced under the effect of a force F exerted along the axis X, by bending of the portion 10 (cf. FIG. 2B).

When the force applied is greater than the pre-strained force, this peripheral portion of the force sensor is displaced to a stop detailed hereafter by compressing the spring washer.

To this end, a space is thus arranged in the direction of the axis X between the bottom 106 of the gear box 100 and the lower surface of the force sensor 1—ball bearing 104—toothed wheel 102 assembly, this space defining a maximum travel of the force sensor 1—ball bearing 104—toothed wheel 102 assembly under the effect of a compressive force. The bottom 106 of the gear box forms the aforementioned stop.

When this stop is reached, the deflection of the sensor is impossible. Furthermore, due to the friction of the toothed wheel 102 against the bottom 106, the movement of the toothed wheel and the gusset is blocked The wave washer, combined with the stop, thus fulfils a security function, intended to protect the sensor against a high compressive force liable to lead to an excessive deflection of the force sensor.

Figure 3A:
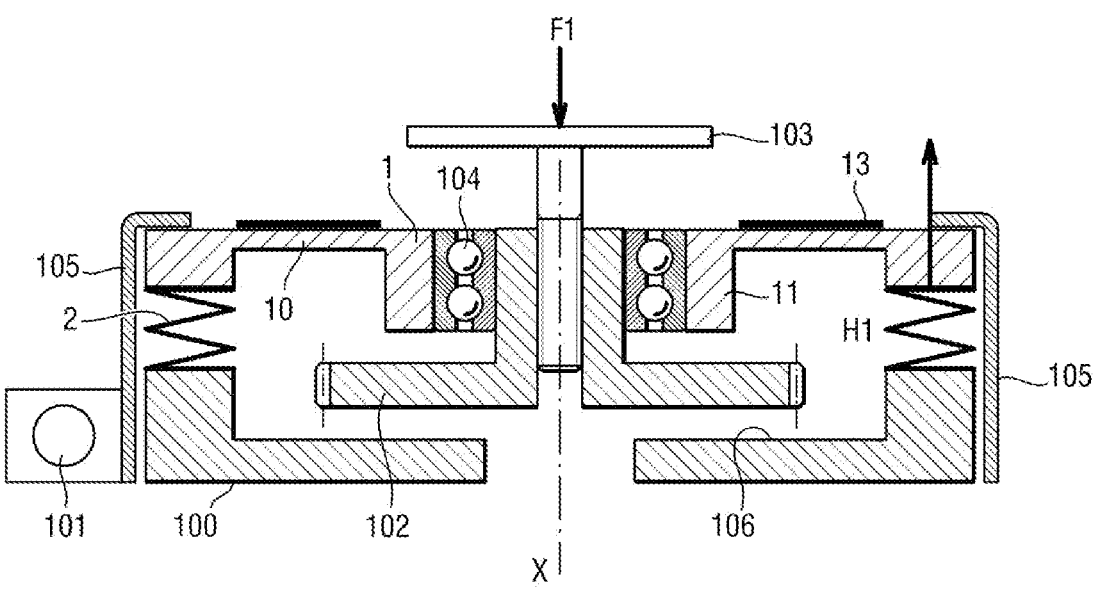
FIG. 3A is a schematic diagram of the security system of the force sensor of FIG. 2B when the compressive force is less than a threshold.
Figure 3B:
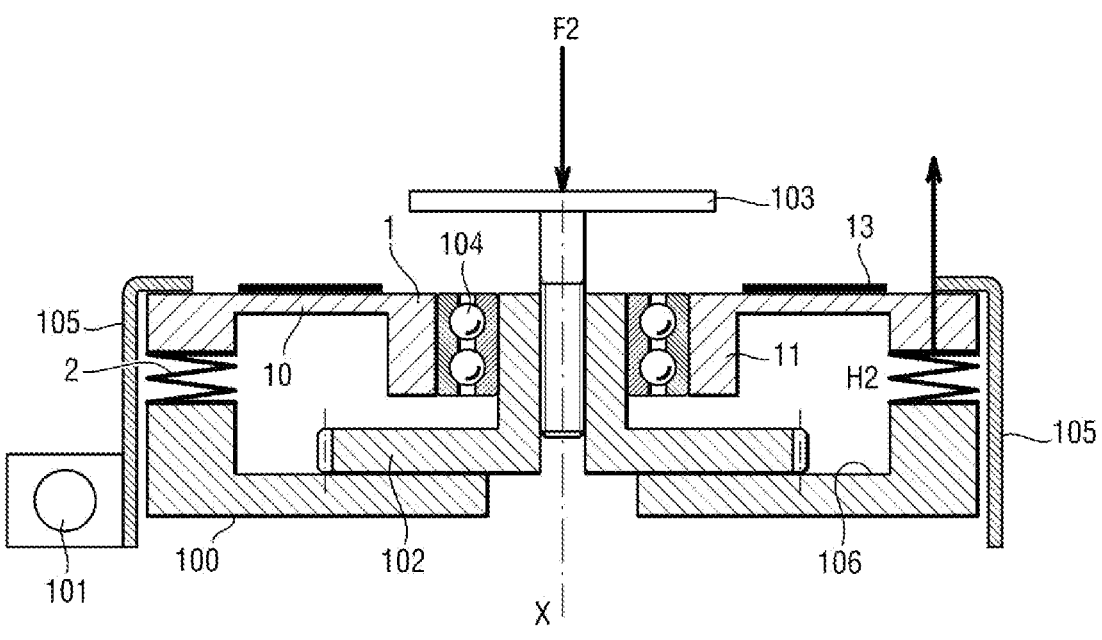
FIG. 3B is a schematic diagram of the security system of the force sensor of FIG. 2B when the compressive force is greater than said threshold.

Indeed, as illustrated in FIG. 3A, as long as the compressive force (noted F1) is less than the value of the pre-strained force of the wave washer, the sensor bends and the deflection generated is measured by the strain gauge 13 to be converted into a force value convertible into pressure value; the height of the wave washer remains equal to the initial height H1 (left view). On the other hand, if the compressive force (noted F2) exceeds said pre-strained value, the force sensor—ball bearing—toothed wheel assembly is displaced along the axis X in the direction of the compressive force, the wave washer is compressed and its height becomes H2 less than H1 (cf. FIG. 3B). The measurement of the force remains possible, but less precise. When the force reaches a certain limit, the sensor—ball bearing—toothed wheel assembly comes to a stop against the bottom 106 of the gear box 100 which makes it possible to limit the displacement of the force sensor—ball bearing—toothed wheel assembly along the axis X in the direction of the compressive force and thus to protect the force sensor (as well as the ball bearing and the stop) against too high compressions which could damage it.

This protection system is active only against excessive compressive forces, typically corresponding to an overpressure of fluid in the variable volume reservoir.

However, as explained above, it is possible to conceive on the same principle a system for protecting the sensor against excessive tractive forces.

Figure 4:
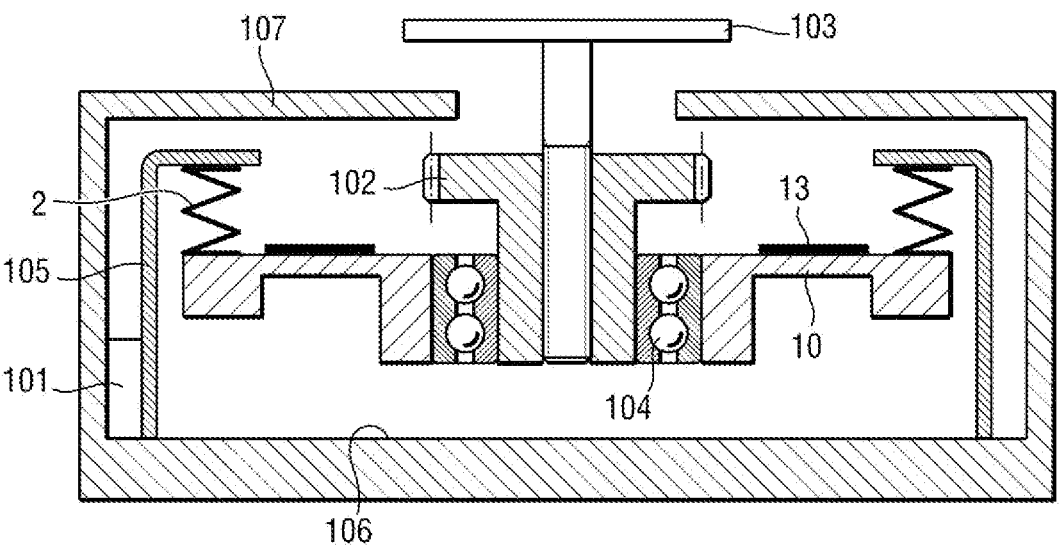
FIG. 4 is a schematic diagram of a second embodiment of the security system of the force sensor in the free state.

Such a system is represented schematically in FIG. 4.

The reference signs identical to those of the preceding figures represent identical components or those fulfilling the same function. Only the aspects specific to the embodiment of FIG. 4 will thus be described here. The elastic element 2 is arranged between the fastening ring 105 and the force sensor 1, in order to bias the force sensor towards the bottom 106 of the gear box, that is to say in the direction opposite to a tractive force. The strain gauge 13 remains positioned at the level of the portion 10 having a restriction in thickness. In this case, the stop may be formed by an upper wall 107 of the gear box opposite to the bottom 106, and is reached when the tractive force is less than the force of deterioration of the sensor.

If necessary, it could be possible to combine the embodiments of FIGS. 2-3 and 4 to protect the force sensor against both excessive traction forces and compressive forces, by implementing two elastic elements and two stops.

Those skilled in the art are able to dimension the wave washer as a function of the force acceptable by the force sensor.

In the document WO 2016/083428, mention is made of a pre-strained system comprising a spring, but this system fulfils a function different to that sought in the present invention. This pre-strained system may be implemented when the sensor only makes it possible to measure compressive forces, in order to create an offset on the force sensor thus also making it possible to measure tractive forces. In fact, in the document WO 2016/083428, this spring is not arranged on the same side of the sensor as the wave washer according to the present invention, and exerts a force of direction opposite to the force exerted by the wave washer. Furthermore, when this pre-strained system is implemented, the sensor is not integral with the moveable part of the fluid reservoir, unlike the present invention.

REFERENCES

WO 2016/083428

The invention claimed is:

1. A system for protecting a force measurement sensor comprising:

the force measurement sensor, designed to measure at least one force exerted along a longitudinal axis of the force measurement sensor, wherein said at least one force comprises a tractive force and/or a compressive force, said force measurement sensor being designed to be made integral with a moveable part of a fluid reservoir, and a pre-strained elastic element arranged to bias the force measurement sensor in a direction opposite to said exerted force, said elastic element being deformable in a direction of the exerted force so as to protect the force measurement sensor from at least one compressive or tractive force greater than a threshold.

2. The system according to claim 1, further comprising a stop, the force measurement sensor being moveable along said longitudinal axis up to said stop in the direction of the force exerted counter to the biasing of the elastic element.

3. The system according to claim 2, wherein the elastic element is pre-strained to a determined force value, designated pre-strained force, said pre-strained force being less than a maximum force being able to be withstood by the force measurement sensor, such that the force measurement sensor is designed to be only displaced towards the stop beyond said pre-strained force.

4. The system according to claim 2, wherein the stop is arranged on a side of the force measurement sensor opposite to the fluid reservoir.

5. The system according to claim 1, further comprising a toothed wheel integral with the force measurement sensor.

6. The system according to claim 1, further comprising a ball bearing integral with the force measurement sensor.

7. The system according to claim 1, wherein the elastic element is arranged on a side of the force measurement sensor opposite to the fluid reservoir.

8. The system according to claim 1, wherein the elastic element is integral with the force measurement sensor.

9. The system according to claim 1, wherein the elastic element is a spring washer.

10. The system according to claim 9, wherein the spring washer is an elastic wave washer.

11. The system according to claim 1, wherein the force measurement sensor comprises an annular portion having a reduction in thickness, the annular portion being capable of bending under the application of an axial force.

12. The system according to claim 11, wherein the elastic element is pre-strained by a peripheral portion of the force measurement sensor external to the annular portion having the reduction in thickness.

13. The system according to claim 11, wherein the force measurement sensor comprises a strain gauge bonded on the annular portion having the reduction in thickness.

14. A medical device designed to be implanted in a human or animal body, comprising:

(a) a fluidic circuit comprising:

an inflatable occlusion cuff containing a variable volume of a fluid, designed to surround at least one part of a natural conduit to occlude, a variable volume reservoir filled with a fluid, said variable volume reservoir comprising a fixed part and a moveable part, a fluidic connection between the variable volume reservoir and the occlusion cuff, (b) an actuator mechanically coupled to the moveable part of the variable volume reservoir so as to linearly displace said moveable part with respect to the fixed part to adjust the volume of the variable volume reservoir, the actuator and the variable volume reservoir being arranged in a sealed housing, (c) the system for protecting a force measurement sensor according to claim 1, the force measurement sensor being integral with the moveable part of the variable volume reservoir.

15. The medical device according to claim 14, wherein the moveable part of the variable volume reservoir is a gusset.

16. The medical device according to claim 15, wherein the gusset comprises a wall integral with a drive screw, the drive screw being coupled by a helical connection to a toothed wheel capable of being rotationally driven by the actuator, the force measurement sensor being arranged around the toothed wheel through a ball bearing.

17. The medical device according to claim 16, wherein the toothed wheel and the force measurement sensor are arranged in a gear box, the force measurement sensor being maintained against the elastic element by a fastening ring.

18. A method for protecting a force measurement sensor designed to measure at least one force exerted along a longitudinal axis of the force measurement sensor, wherein said at least one force comprises a tractive force and/or a compressive force, said force measurement sensor being designed to be made integral with a moveable part of a fluid reservoir, the method comprising at least:

providing the system for protecting said force measurement sensor according to claim 1, exerting the at least one tractive or one compressive force along the longitudinal axis of the force measurement sensor such that (i) as long as said the at least one tractive or one compressive force is less than a pre-strained force of the elastic element, the force measurement sensor deforms to measure the at least one tractive or one compressive force and (ii) when said the at least one tractive or one compressive force becomes greater than said pre-strained force, the force measurement sensor is displaced up to a stop.

19. The method according to claim 18, wherein the force measurement sensor reaches the stop when the at least one tractive or one compressive force is less than a force of deterioration of the force measurement sensor.

20. The method according to claim 18, wherein the force measurement sensor is only displaced towards the stop beyond the pre-strained force.

* * * * *